(12) United States Patent
Shelton, IV

(10) Patent No.: US 7,784,663 B2
(45) Date of Patent: Aug. 31, 2010

(54) SURGICAL STAPLING INSTRUMENT HAVING LOAD SENSING CONTROL CIRCUITRY

(75) Inventor: Frederick E. Shelton, IV, Hillsboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 479 days.

(21) Appl. No.: 11/240,836

(22) Filed: Sep. 30, 2005

(65) Prior Publication Data

US 2006/0212069 A1      Sep. 21, 2006

Related U.S. Application Data

(63) Continuation-in-part of application No. 11/082,495, filed on Mar. 17, 2005, now Pat. No. 7,506,790.

(51) Int. Cl.
    *A61B 17/068* (2006.01)
(52) U.S. Cl. .............. 227/175.1; 227/19; 227/175.2; 227/180.1; 606/139; 606/219
(58) Field of Classification Search .......... 227/19, 227/175.1, 176.1, 175.2, 175.3, 178.1, 180.1; 606/139, 219
See application file for complete search history.

(56) References Cited

U.S. PATENT DOCUMENTS

| | | |
|---|---|---|
| 2,711,461 A | 6/1955 | Happe |
| 4,473,077 A | 9/1984 | Noiles et al. |
| 4,543,090 A | 9/1985 | McCoy |
| 4,554,064 A | 11/1985 | McClintock et al. |
| 4,601,705 A | 7/1986 | McCoy |
| 4,753,223 A | 6/1988 | Bremer |
| 4,892,545 A | 1/1990 | Day et al. |
| 5,031,814 A | 7/1991 | Tompkins et al. |
| 5,071,052 A | 12/1991 | Rodak et al. |
| 5,137,198 A | 8/1992 | Nobis et al. |
| 5,171,249 A | 12/1992 | Stefanchik et al. |
| 5,202,914 A | 4/1993 | Kim et al. |
| 5,263,629 A | 11/1993 | Trumbull et al. |
| 5,290,240 A * | 3/1994 | Horres, Jr. .................. 604/131 |
| 5,312,023 A | 5/1994 | Green et al. |
| 5,372,124 A | 12/1994 | Takayama et al. |
| 5,387,194 A * | 2/1995 | Williams et al. ......... 604/97.03 |

(Continued)

FOREIGN PATENT DOCUMENTS

DE      1993372      9/1968

(Continued)

OTHER PUBLICATIONS

EPO Search Report, Application No. 05254680.1, Jan. 12, 2006, pp. 1-5.

(Continued)

*Primary Examiner*—Scott A. Smith
(74) *Attorney, Agent, or Firm*—Frost Brown Todd LLC

(57) ABSTRACT

A surgical instrument for being endoscopically or laparoscopically inserted into a surgical site for simultaneous stapling and severing of tissue includes load sensing pressure transducers strategically placed for closed loop control and monitoring. Load sensing within a staple applying assembly (end effector) may provide feedback for preventing firing with insufficient or too much tissue, or to sense appropriate presence buttress material, to deploy buttress material after firing is sensed.

30 Claims, 9 Drawing Sheets

U.S. PATENT DOCUMENTS

| | | | |
|---|---|---|---|
| 5,389,098 A | 2/1995 | Tsuruta et al. |
| 5,397,046 A | 3/1995 | Savage et al. |
| 5,397,324 A | 3/1995 | Carroll et al. |
| 5,399,256 A | 3/1995 | Bohs et al. |
| 5,403,312 A | 4/1995 | Yates et al. |
| 5,413,267 A | 5/1995 | Solyntjes et al. |
| 5,413,268 A | 5/1995 | Green et al. |
| 5,431,668 A | 7/1995 | Burbank, III et al. |
| 5,441,193 A | 8/1995 | Gravener |
| 5,445,304 A | 8/1995 | Plyley et al. |
| 5,465,895 A | 11/1995 | Knodel et al. |
| 5,468,250 A | 11/1995 | Paraschac et al. |
| 5,484,095 A | 1/1996 | Green et al. |
| 5,503,638 A | 4/1996 | Cooper et al. |
| 5,520,787 A | 5/1996 | Hanagan et al. |
| 5,535,937 A | 7/1996 | Boiarski et al. |
| 5,542,594 A | 8/1996 | McKean et al. |
| 5,549,628 A | 8/1996 | Cooper et al. |
| 5,555,555 A | 9/1996 | Sato et al. |
| 5,562,239 A | 10/1996 | Boiarski et al. |
| 5,584,425 A | 12/1996 | Savage et al. |
| 5,592,668 A | 1/1997 | Harding et al. |
| 5,599,329 A | 2/1997 | Gabbay |
| 5,601,582 A | 2/1997 | Shelton, IV et al. |
| 5,609,285 A | 3/1997 | Grant |
| 5,624,452 A | 4/1997 | Yates |
| 5,634,584 A | 6/1997 | Okorocha et al. |
| 5,635,721 A | 6/1997 | Bardi et al. |
| 5,661,887 A * | 9/1997 | Byrne et al. ............ 29/243.525 |
| 5,665,285 A | 9/1997 | Hattori et al. |
| 5,667,517 A | 9/1997 | Hooven |
| 5,669,918 A | 9/1997 | Balaz |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,409 A | 12/1997 | Rayburn et al. |
| 5,704,534 A | 1/1998 | Huitema et al. |
| 5,709,334 A | 1/1998 | Sorrentino et al. |
| 5,735,445 A | 4/1998 | Vidal et al. |
| 5,769,892 A | 6/1998 | Kingwell |
| 5,779,130 A | 7/1998 | Alesi et al. |
| 5,792,165 A | 8/1998 | Klieman et al. |
| 5,797,537 A | 8/1998 | Oberlin et al. |
| 5,810,855 A | 9/1998 | Rayburn et al. |
| 5,826,776 A | 10/1998 | Schulze et al. |
| 5,829,662 A | 11/1998 | Allen et al. |
| 5,855,565 A * | 1/1999 | Bar-Cohen et al. .......... 604/104 |
| 5,865,361 A | 2/1999 | Milliman et al. |
| 5,876,401 A | 3/1999 | Schulze et al. |
| 5,901,895 A | 5/1999 | Heaton et al. |
| 5,902,312 A | 5/1999 | Frater et al. |
| 5,908,427 A | 6/1999 | McKean et al. |
| 5,918,791 A | 7/1999 | Sorrentino et al. |
| 5,959,852 A | 9/1999 | Deloy et al. |
| 5,964,774 A | 10/1999 | McKean et al. |
| 5,972,165 A | 10/1999 | Sethna et al. |
| 6,010,054 A | 1/2000 | Johnson et al. |
| 6,032,849 A | 3/2000 | Mastri et al. |
| 6,033,427 A | 3/2000 | Lee |
| 6,063,097 A | 5/2000 | Oi et al. |
| 6,079,606 A | 6/2000 | Milliman et al. |
| 6,109,500 A | 8/2000 | Alli et al. |
| 6,202,914 B1 | 3/2001 | Geiste et al. |
| 6,241,139 B1 | 6/2001 | Milliman |
| 6,302,311 B1 | 10/2001 | Adams et al. |
| 6,330,965 B1 | 12/2001 | Milliman et al. |
| 6,488,197 B1 | 12/2002 | Whitman |
| 6,494,896 B1 | 12/2002 | D'Alessio et al. |
| 6,503,257 B2 | 1/2003 | Grant et al. |
| 6,503,259 B2 * | 1/2003 | Huxel et al. ................. 606/153 |
| 6,514,237 B1 | 2/2003 | Maseda |
| 6,545,384 B1 | 4/2003 | Pelrine et al. |
| 6,577,899 B2 * | 6/2003 | Lebel et al. ................... 607/60 |
| 6,583,533 B2 | 6/2003 | Pelrine et al. |
| 6,586,859 B2 | 7/2003 | Kornbluh et al. |
| 6,652,521 B2 | 11/2003 | Schulze |
| 6,656,193 B2 | 12/2003 | Grant et al. |
| 6,667,825 B2 | 12/2003 | Lu et al. |
| 6,699,245 B2 | 3/2004 | Dinger et al. |
| 6,716,233 B1 | 4/2004 | Whitman |
| 6,740,079 B1 * | 5/2004 | Eggers et al. ................. 606/34 |
| 6,770,027 B2 | 8/2004 | Banik et al. |
| 6,830,174 B2 | 12/2004 | Hillstead et al. |
| 6,835,173 B2 | 12/2004 | Couvillon, Jr. |
| 6,840,246 B2 * | 1/2005 | Downing .................... 128/898 |
| 6,905,057 B2 | 6/2005 | Swayze et al. |
| 6,913,579 B2 | 7/2005 | Truckai et al. |
| 6,923,804 B2 | 8/2005 | Eggers et al. |
| 6,959,852 B2 | 11/2005 | Shelton, IV et al. |
| 6,964,363 B2 | 11/2005 | Wales et al. |
| 6,969,395 B2 * | 11/2005 | Eskuri ......................... 606/200 |
| 6,978,921 B2 | 12/2005 | Shelton, IV et al. |
| 6,981,628 B2 | 1/2006 | Wales |
| 6,988,649 B2 | 1/2006 | Shelton, IV et al. |
| 7,000,819 B2 | 2/2006 | Swayze et al. |
| 7,044,352 B2 | 5/2006 | Shelton IV et al. |
| 7,055,731 B2 | 6/2006 | Shelton, IV |
| 7,063,699 B2 | 6/2006 | Hess et al. |
| 7,074,217 B2 * | 7/2006 | Strul et al. ..................... 606/41 |
| 7,083,075 B2 | 8/2006 | Swayze et al. |
| 7,111,769 B2 | 9/2006 | Wales et al. |
| 7,140,528 B2 * | 11/2006 | Shelton, IV .............. 227/175.4 |
| 7,143,925 B2 * | 12/2006 | Shelton et al. ........... 227/175.2 |
| 7,147,138 B2 * | 12/2006 | Shelton, IV .............. 227/176.1 |
| 7,208,005 B2 | 4/2007 | Frecker et al. |
| 7,213,736 B2 | 5/2007 | Wales et al. |
| 7,238,195 B2 | 7/2007 | Viola |
| 7,320,700 B2 | 1/2008 | Cooper et al. |
| 7,338,509 B2 | 3/2008 | Mattison |
| 7,354,447 B2 | 4/2008 | Shelton et al. |
| 7,364,061 B2 | 4/2008 | Swayze et al. |
| 7,367,485 B2 | 5/2008 | Shelton, IV et al. |
| 7,380,696 B2 | 6/2008 | Shelton, IV et al. |
| 7,404,509 B2 | 7/2008 | Ortiz et al. |
| 7,407,074 B2 | 8/2008 | Ortiz et al. |
| 7,431,730 B2 | 10/2008 | Viola |
| 7,517,356 B2 | 4/2009 | Heinrich |
| 7,559,452 B2 | 7/2009 | Wales et al. |
| 7,607,557 B2 | 10/2009 | Shelton et al. |
| 2001/0029384 A1 | 10/2001 | Nicholas et al. |
| 2002/0074005 A1 | 6/2002 | Hogg et al. |
| 2002/0165541 A1 | 11/2002 | Whitman |
| 2003/0065358 A1 | 4/2003 | Frecker |
| 2003/0069474 A1 | 4/2003 | Couvillon, Jr. |
| 2003/0199870 A1 | 10/2003 | Truckai et al. |
| 2003/0236531 A1 | 12/2003 | Couvillon, Jr. |
| 2004/0002726 A1 | 1/2004 | Nunez et al. |
| 2004/0054322 A1 | 3/2004 | Vargas |
| 2004/0068224 A1 | 4/2004 | Danda et al. |
| 2004/0097971 A1 | 5/2004 | Hughett |
| 2004/0138700 A1 | 7/2004 | Cooper et al. |
| 2004/0149802 A1 | 8/2004 | Whitman |
| 2004/0193190 A1 | 9/2004 | Liddicoat |
| 2004/0232195 A1 | 11/2004 | Shelton, IV et al. |
| 2004/0232196 A1 | 11/2004 | Shelton et al. |
| 2004/0232197 A1 | 11/2004 | Shelton et al. |
| 2005/0006429 A1 | 1/2005 | Wales et al. |
| 2005/0006431 A1 | 1/2005 | Shelton et al. |
| 2005/0006434 A1 | 1/2005 | Wales et al. |
| 2005/0067457 A1 | 3/2005 | Shelton et al. |
| 2005/0067458 A1 | 3/2005 | Swayze et al. |

| | | | |
|---|---|---|---|
| 2005/0085693 | A1 | 4/2005 | Belson et al. |
| 2005/0102017 | A1 | 5/2005 | Mattison |
| 2005/0165415 | A1 | 7/2005 | Wales |
| 2005/0173490 | A1 | 8/2005 | Shelton |
| 2006/0016853 | A1 | 1/2006 | Racenet |
| 2006/0022014 | A1 | 2/2006 | Shelton, IV et al. |
| 2006/0022015 | A1 | 2/2006 | Shelton, IV et al. |
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton et al. |
| 2006/0025816 | A1 | 2/2006 | Shelton, IV |
| 2006/0060630 | A1 | 3/2006 | Shelton, IV et al. |
| 2006/0190028 | A1 | 8/2006 | Wales et al. |
| 2007/0102453 | A1 | 5/2007 | Morgan et al. |

FOREIGN PATENT DOCUMENTS

| | | |
|---|---|---|
| DE | 4015562 | 11/1991 |
| DE | 4303544 | 9/1993 |
| DE | 19534320 | 2/1997 |
| DE | 19537299 | 4/1997 |
| DE | 19643073 | 4/1997 |
| DE | 19647354 | 5/1998 |
| EP | 0 500 353 | 8/1992 |
| EP | 0 674 876 | 10/1995 |
| EP | 0 741 996 | 11/1996 |
| EP | 0741966 | 11/1996 |
| EP | 0 832 605 | 4/1998 |
| EP | 1323384 | 7/2003 |
| EP | 1 522 264 | 4/2005 |
| EP | 1621137 | 2/2006 |
| EP | 1621141 | 2/2006 |
| EP | 1621143 | 2/2006 |
| EP | 1621151 | 2/2006 |
| EP | 1693008 | 8/2006 |
| WO | WO 99/02090 | 1/1999 |
| WO | WO 00/78222 | 12/2000 |
| WO | WO 01/56455 | 8/2001 |
| WO | WO 01/62158 | 8/2001 |
| WO | WO 01/62163 | 8/2001 |
| WO | WO 02/28268 | 4/2002 |
| WO | WO 03/088845 | 10/2003 |
| WO | WO 03/090630 | 11/2003 |
| WO | WO 03/094743 | 11/2003 |
| WO | WO 2004/014238 | 2/2004 |
| WO | WO 2004/050971 | 6/2004 |
| WO | WO 2004/086987 | 10/2004 |

OTHER PUBLICATIONS

EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
EPO Search Report, Application No. 06255062.9, Nov. 23, 2006, pp. 1-3.
EPO Search Report, Application No. 06255053.8, Jan. 25, 2007, pp. 1-3.
EPO Search Report, Application No. 06255057.9, Jan. 29, 2007, pp. 1-3.
EPO Search Report, Application No. 06255058.7, Jan. 31, 2007, pp. 1-3.
EPO Search Report, Application No. 06255064.5, Feb. 9, 2007, pp. 1-3.
EPO Search Report, Application No. 06255065.2, Feb. 15, 2007, pp. 1-3.
U.S. Appl. No. 60/591,694, filed Jul. 28, 2004, Shelton IV, Frederick E.
U.S. Appl. No. 10/441,424, filed May 20, 2003, Shelton, et al.
U.S. Appl. No. 10/443,617, filed May 20, 2003, Shelton, et al.
U.S. Appl. No. 10/615,971, filed Jul. 9, 2003, Wales, et al.
U.S. Appl. No. 10/615,973, filed Sep. 29, 2003, Shelton, et al.
U.S. Appl. No. 10/673,929, filed Sep. 29, 2003, Shelton, et al.
U.S. Appl. No. 10/052,387, filed Feb. 8, 2005, Shelton, et al.
U.S. Appl. No. 11/052,632, filed Feb. 8, 2008, Swayze, et al.
U.S. Appl. No. 11/066,371, filed Feb. 25, 2005, Shelton, et al.
U.S. Appl. No. 11/082,495, filed Mar. 17, 2005, Shelton, et al.
U.S. Appl. No. 11/083,740, filed May 8, 2007, Wales, Kenneth.
U.S. Appl. No. 11/162,984, Sep. 30, 2005, Ortiz, Mark.
U.S. Appl. No. 11/162,985, Sep. 30, 2005, Ortiz, Mark.
U.S. Appl. No. 11/162,986, Sep. 30, 2005, Ortiz, Mark.
U.S. Appl. No. 11/162,988, Sep. 30, 2005, Ortiz, Mark.
U.S. Appl. No. 11/162,990, Sep. 30, 2005, Ortiz, Mark.
U.S. Appl. No. 11/162,991, Sep. 30, 2005, Ortiz, Mark.
U.S. Appl. No. 11/162,992, Sep. 30, 2005, Ortiz, Mark.
European Search Report for EPO Application No. 06255053, dated. Jan. 25, 2007.
Notice of Allowance for U.S. Appl. No. 11/096,158 dated May 23, 2006.
Notice of Allowance for U.S. Appl. No. 11/066,371 dated Jul. 25, 2006.
Notice of Allowance for U.S. Appl. No. 11/157,767 dated Aug. 14, 2006.
Notice of Allowance for U.S. Appl. No. 11/181,471 dated Aug. 22, 2006.
Notice of Allowance for U.S. Appl. No. 11/083,740 dated Sep. 25, 2006.
Non-Final Rejection for U.S. Appl. No. 11/181,046, dated Nov. 13, 2006.
Non-Final Rejection for U.S. Appl. No. 11/082,495, dated Mar. 22, 2007.
Non-Final Rejection for U.S. Appl. No. 11/162,990, dated Aug. 7, 2007.
Non-Final Rejection for U.S. Appl. No. 11/181,046, dated Aug. 29, 2007.
Notice of Allowance for U.S. Appl. No. 11/096,096 dated Aug. 31, 2007.
Notice of Allowance for U.S. Appl. No. 11/240,836, dated Sep. 12, 2007.
Notice of Allowance for U.S. Appl. No. 11/082,495, dated Sep. 19, 2007.
Non Final Rejection for U.S. Appl. No. 11/162,986, dated Sep. 21, 2007.
Non-Final Rejection for U.S. Appl. No. 11/162,988, dated Sep. 21, 2007.
U.S. Appl. No. 10/441,362, filed May 20, 2003, Ho.
Notice of Allowance dated Sep. 19, 2007 for U.S. Appl. No. 11/082,495.
Notice of Allowance dated Oct. 1, 2007 for U.S. Appl. No. 10/955,042.
Office Action dated Mar. 15, 2006 for U.S. Appl. No. 10/955,042.
Office Action dated Mar. 22, 2007 for U.S. Appl. No. 11/082,495.
Office Action dated Mar. 29, 2007 for U.S. Appl. No. 10/955,042.
Final Rejection dated Oct. 18, 2006 for U.S. Appl. No. 11/096,096.
Notice of Allowance dated Dec. 1, 2006 for U.S. Appl. No. 10/955,042.
Notice of Allowance dated Jan. 5, 2007 for U.S. Appl. No. 11/096,096.
Notice of Allowance dated Mar. 25, 2008 for U.S. Appl. No. 11/096,096.
Notice of Allowance dated Apr. 10, 2008 for U.S. Appl. No. 11/082,495.
Notice of Allowance dated Apr. 18, 2008 for U.S. Appl. No. 11/162,985.
Notice of Allowance dated Apr. 18, 2008 for U.S. Appl. No. 11/162,986.
Notice of Allowance dated Apr. 18, 2008 for U.S. Appl. No. 11/162,988.
Non-Final Rejection dated May 5, 2008 for U.S. Appl. No. 11/181,046.
Notice of Allowance dated Jun. 10, 2008 for U.S. Appl. No. 11/082,495.
Notice of Allowance dated Aug. 11, 2008 for U.S. Appl. No. 11/082,495.

EPO Search Report dated Feb. 29, 2008 for Application No. 05254681.9.
EPO Search Report dated Mar. 3, 2008 for Application No. 05254699.1.
EPO Search Report dated Feb. 26, 2008 for Application No. 05254700.7.
EPO Search Report dated Mar. 25, 2008 for Application No. 05254703.1.
Guidelines for Hand and Power Tools, http://www.osha.gov/doc/outreachtraining/htmlfiles/tools.html, OSHA, May 1996, p. 3.

European Search Report dated Mar. 27, 2008 for Application 05254684.
Abstract - DE 4015562.
Abstract - DE 4303544.
Abstract - DE 19534320.
Abstract - DE 19537299.
Abstract - DE 19643073.
Abstract - DE 19647354.

* cited by examiner

SURGICAL STAPLING INSTRUMENT HAVING LOAD SENSING CONTROL CIRCUITRY

CROSS REFERENCE TO RELATED APPLICATIONS

This application is a Continuation in Part of U.S. patent application Ser. No. 11/082,495, entitled "Surgical Instrument Incorporating an Electrically Acutated Articulation Mechanism", filed on Mar. 17, 2005, the disclosure of which is hereby incorporated by reference in its entirety.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments including adding bolstering material to the severed and stapled tissue.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures have been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Small videoscopes of various types (e.g., endoscopes) are relied upon to monitor proper positioning and operation of the surgical stapler. While effective to a degree, it is desirable to have improved monitoring of operation of the surgical stapler, especially if such monitoring enables closed loop control of various actuations performed by the surgical stapler.

Consequently, a significant need exists for an improved surgical stapling and severing instrument that incorporates a load sensing capability.

BRIEF SUMMARY OF THE INVENTION

The invention overcomes the above-noted and other deficiencies of the prior art by providing a surgical instrument that incorporates an electrical pressure sensor positioned to receive a compressive load when the surgical instrument is actuated. Control circuitry that monitors the electrical pressure sensor then generates a control signal responsive to that sensed compressive load to enhance operation of the surgical instrument.

In one aspect of the invention, a surgical instrument has a staple applying assembly with first and second opposing compression surfaces that clamp tissue to be stapled and imparts a compressive force thereby to a pressure transducer. The staple applying assembly is closed by a handle portion and actuated by a firing member moved by the handle portion through a shaft. Control circuitry responds to the sensed compression load of the staple applying assembly to send a control signal to an electrical actuator. Thereby, a desired sequence of events may be enforced that are dependent upon first successfully clamping a desired amount of tissue, avoiding dry firing of an actuator in the absence of sufficient tissue or ineffective activation of the actuator in the presence of too much tissue.

In another aspect of the invention, a surgical instrument has an end effector that is attached to a shaft and in turn to a handle portion. A firing member is translated by the handle portion and received for longitudinal reciprocation in the shaft to actuate the end effector and to thereby impart a compressive load upon a pressure transducer. Control circuitry is responsive to a signal received from the pressure transducer to generate a control signal. Thereby, a desired sequence of events may be enforced that are dependent upon firing having commenced or having been successfully completed.

In yet another aspect of the invention, a surgical instrument has an articulated shaft that allows for articulating an end effector. Control circuitry receives a signal from a sensor in an articulation joint of the shaft that is representative of an articulation angle so that a control signal may be generated. Thereby, a desired sequence of events may be enforced that are dependent upon achieving a desired angle of articulation of the shaft and end effector.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
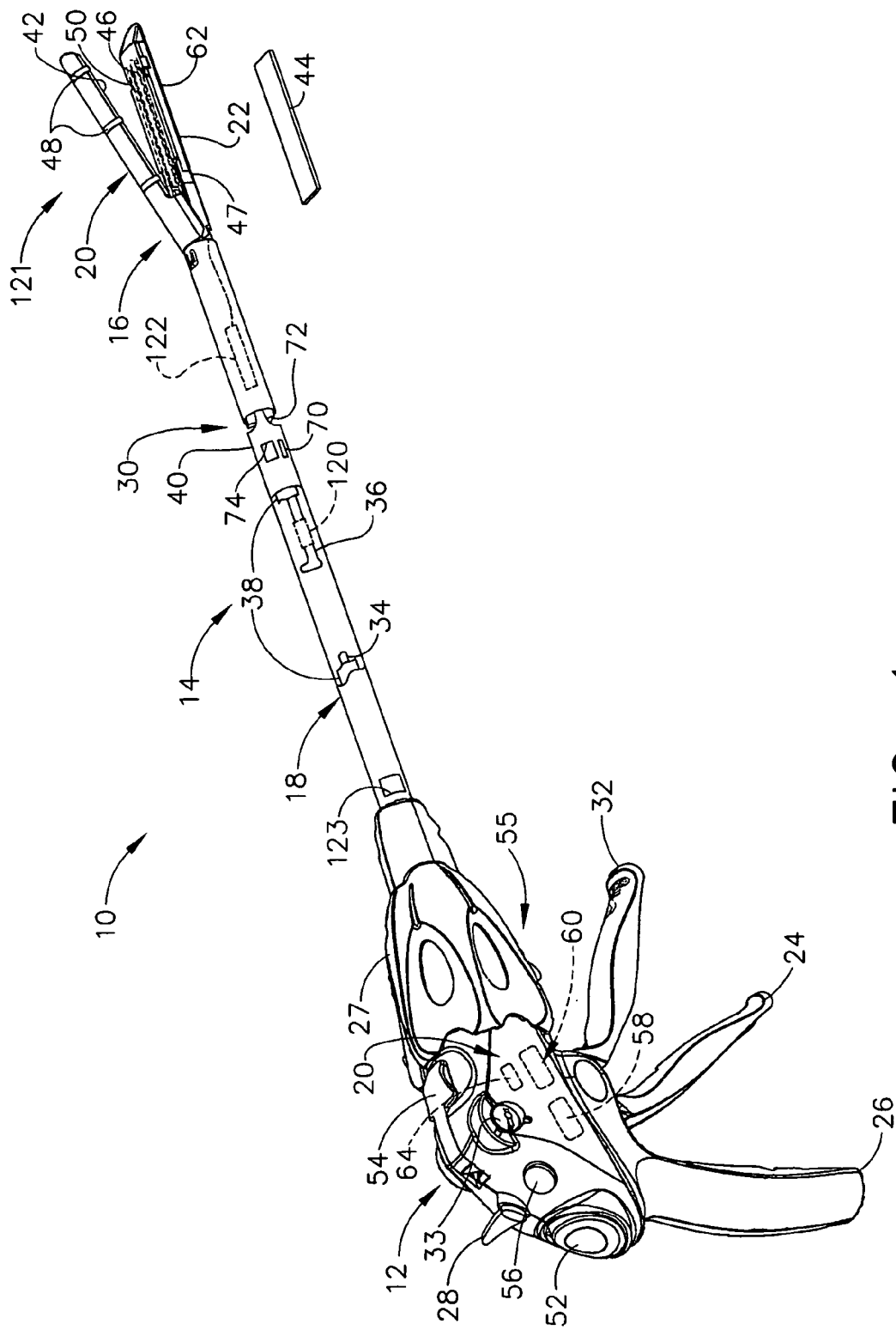
FIG. 1 depicts a partially cutaway side elevation view of a surgical stapling and severing instrument with a staple applying assembly in an open position, a lower buttress pad removed to expose a staple cartridge, and an elongate shaft partially cutaway to expose components of a closed loop control system consistent with the present invention including components in a handle portion shown in phantom.

Turning to the Drawings, wherein like numerals denote like components throughout the several views, in FIG. 1, a surgical stapling and severing instrument 10 includes a handle portion 12 that manipulates to position an implement portion 14 formed from a fastening end effector, specifically a staple applying assembly 16, distally attached to an elongate shaft 18. The implement portion 14 is sized for insertion through a cannula of a trocar (not shown) for an endoscopic or laparoscopic surgical procedure with an upper jaw (anvil) 20 and a lower jaw 22 of the staple applying assembly 16 closed by depression of a closure trigger 24 toward a pistol grip 26 of the handle portion 12.

Once inserted into an insufflated body cavity or lumen, the surgeon may rotate the implement portion 14 about its longitudinal axis by twisting a shaft rotation knob 27 that engages across a distal end of the handle 12 and a proximal end of the elongate shaft 18. The surgeon may selectively move to either lateral side an articulation control lever 28 on the handle portion 12 to cause a distal portion of the elongate shaft 18 and the staple applying assembly 16 to articulate about an articulation joint 30. Thereby, the staple applying assembly 16 may approach tissue otherwise obscured by other tissue or allow for an endoscope to be positioned behind the staple applying assembly 16. Thus positioned, the closure trigger 24 may be released, opening the anvil 20 so that tissue may be grasped and positioned. Once satisfied, the surgeon depresses the closure trigger 24 until locked against the pistol grip 26, clamping the staple applying assembly 16. Then a firing trigger 32 is depressed, perhaps multiple times referencing firing progress on a firing indicator gauge 33. The firing trigger 32 is drawn toward the closure trigger 24 and pistol grip 26, thereby distally advancing a firing member, depicted as including a proximal firing rod 34 attached to a distal firing bar 36, that is supported within a frame ground assembly 38 that connects the handle portion 12 to the staple applying assembly 16. An outer closure sleeve 40 longitudinally translates upon the frame ground assembly 38 to pivot the anvil 20 in response to the closure trigger 24.

To assist in stapling a thin layer and/or a thick layer of tissue, buttress material of an upper buttress pad 42 and a lower buttress pad 44 may be held on each inner surface of the anvil 20 and upon a staple cartridge 46 engaged within an elongate staple channel 47 of the lower jaw 22. After firing of the staple applying assembly 16, the buttress pads 42, 44 which are severed and stapled along with the clamped tissue, are disengaged by actuating upper and lower buttress clamps 48, 50 to remain with the two stapled and severed ends of tissue as the firing trigger 32 is released and a closure release button 52 is depressed to unlock the closure trigger 24 to open the staple applying assembly 16.

It should be appreciated that a distal end of the firing bar 36 includes or is coupled to a knife that traverses a vertical slot in the staple cartridge 46 to sever clamped tissue and the buttress pads 42, 44. The knife is coupled to a wedge assembly that cams staples upwardly out of the staple cartridge 46 through the clamped tissue and buttress pads 42, 44 to close and form against the anvil 20. Thereafter, the firing bar 36 is withdrawn by an end-of-firing-travel release mechanism and a retraction bias in the handle portion 12. The surgeon may abort after partial firing and/or effect manual retraction of the firing member 34, 36 by actuating a manual retraction lever 54 on the top of the handle portion 12.

Figure 2:
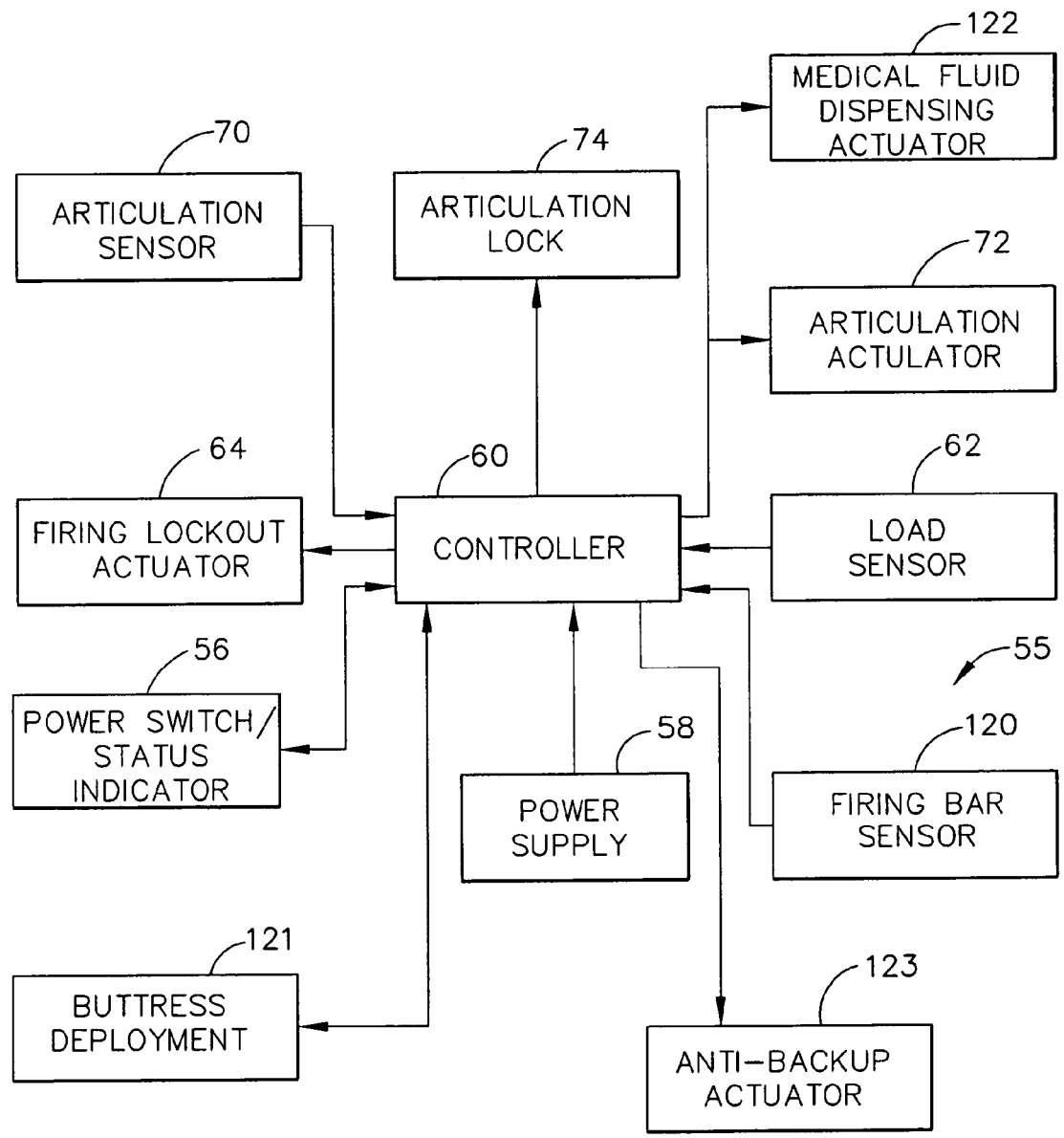
FIG. 2 is a block diagram of the closed loop control circuitry of the surgical stapling and severing instrument of FIG. 1.

In FIGS. 1-2, consistent with the present invention, a closed loop control system 55 enhances operation of the surgical stapling and severing instrument 10 by monitoring proper operation and electrically controlling various features. A power switch 56 may be depressed by the user to activate the closed loop control system 55, drawing upon a power supply, depicted as a battery 58. A visual confirmation (status indicator) on the handle portion 12 may be incorporated into power switch 56 to indicate what the state of the closed loop control system 55 (e.g., color/flash illumination and/or alphanumeric message of the power button 56), such as "POWER ON", "OPERATIONAL-SELF-TEST PASSED", "LOAD STAPLE CARTRIDGE", "LOAD BUTTRESS PADS", "SYSTEM LOADED/AWAITING FIRING", "FAULT DETECTED", etc. Additional programming flexibility may be achieved by incorporating a wired or wireless (e.g., BLUETOOTH) protocol to interface the closed loop control system 55 to an external graphical user interface (e.g., personal computer).

Figure 3:
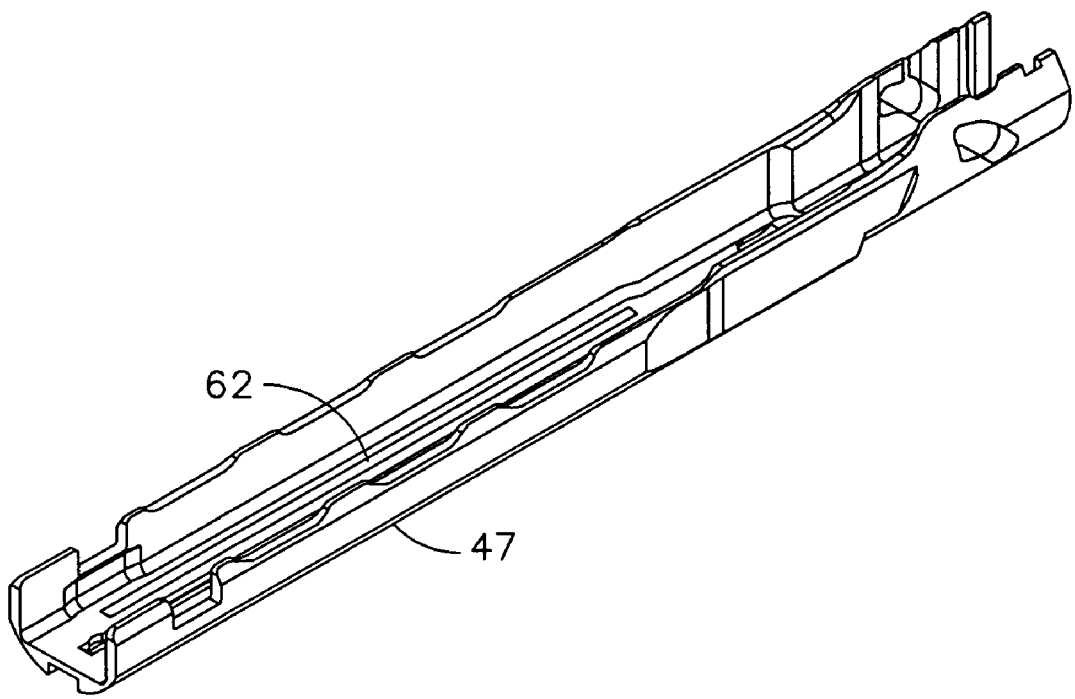
FIG. 3 is a left front isometric view of an elongate staple channel of the staple applying assembly of FIG. 1 incorporating elongate electroactive polymer (EAP) sensor strips for load sensing.

The closed loop control system 55 includes a controller 60 that advantageously receives signals from electrical sensors that monitor operation of the surgical stapling and severing instrument 10. In particular, a load sensor, such as an elongate electroactive polymer (EAP) load strip 62 (FIG. 3) or aligned series of EAP strips 63 (FIG. 4) between the staple cartridge 46 and the elongate staple channel 47, monitors the amount of clamping force in the staple applying assembly 16. Determination that a proper clamping force has been achieved may then be used as a condition precedent by the controller 60 before firing, such as by activating a firing lockout actuator 64 that prevents inadvertent firing.

A useful feature of EAP is its sensing (transduction) capabilities. For instance, an excellent dynamic response (sensing mode) may be achieved with an EAP strip in a loaded cantilever form. A damped electric response is observed that is highly repeatable with a high bandwidth up to about 100 Hz. Such direct mechanoelectric behaviors are related to the endo-ionic mobility due to imposed stresses. It means that, if we impose a finite soft-phase flux but do not allow a current flux, it creates a certain conjugate electric field that can be dynamically monitored. In this sense, EAP is truly multifunctional: structural, actuating, and sensing capabilities in one body. EAP actuators are described in greater detail below.

Illustrative firing lockout actuators 64 may be incorporated into the handle portion 12 as described in co-pending and commonly owned U.S. patent application Ser. No. 11/095,428 entitled "Surgical Instrument Incorporating EAP Complete Firing System Lockout Mechanism" and filed on Mar. 31, 2005, the disclosure of which is hereby incorporated by reference in its entirety. Alternatively or in addition, firing lockout actuators 64 may be incorporated into the implement portion 14 as described in co-pending and commonly owned U.S. patent application Ser. No. 11/066,371 entitled "Surgical Stapling Instrument Having An Electroactive Polymer Actuated Single Lockout Mechansim For Prevention Of Firing" and filed on Feb. 25, 2005, the disclosure of which is hereby incorporated by reference in its entirety.

Continuing with FIGS. 1-2, the controller 60 also receives a signal from one or more articulation sensors 70. The signal is responsive to an angle of articulation of the articulation joint, either continuously and/or a discrete articulation limit threshold. This information may be used to perform closed loop control of an articulation actuator 72. Illustrative versions of electrically actuated articulation are described in three co-pending and commonly-owned patent applications (1) U.S. patent application Ser. No. 11/082,495 entitled "Surgical Instrument Incorporating an Electrically Actuated Articulation Mechanism" and filed on Mar. 17, 2005; (2) U.S. patent application Ser. No. 11/096,096 entitled "Surgical Instrument Incorporating an Electrically Actuated Pivoting Articulation Mechanism" and filed on Mar. 31, 2005; and (3) U.S. patent application Ser. No. 11/096,158 entitled "Surgical Instrument Incorporating an Electrically Actuated Articulation Mechanism" and filed on Mar. 31, 2005, the disclosures of which are hereby incorporated by reference in their entirety. Once at a desired articulation angle, the controller 60 may reengage an electrically actuated articulation lock 74 to maintain the articulation. An illustrative articulation lock is described in co-pending and commonly-owned U.S. patent application Ser. No. 11/092,053 entitled "Surgical Instrument Incorporating an Electrically Actuated Articulation Locking Mechanism", filed on Mar. 29, 2005, the disclosure of which is hereby incorporated by reference in its entirety.

It should be appreciated given the benefit of the present disclosure that applications consistent with the present invention may incorporate a mechanically articulated and/or mechanically locked shaft rather than an electrical articulated and/or electrically locked shaft. Moreover, a control signal from the controller 60 may merely provide a visual and/or aural indication to the user confirming that the desired articulation angle has been achieved so a command to further articulate may be discontinued and/or the articulation joint may be manually locked.

Figure 4:
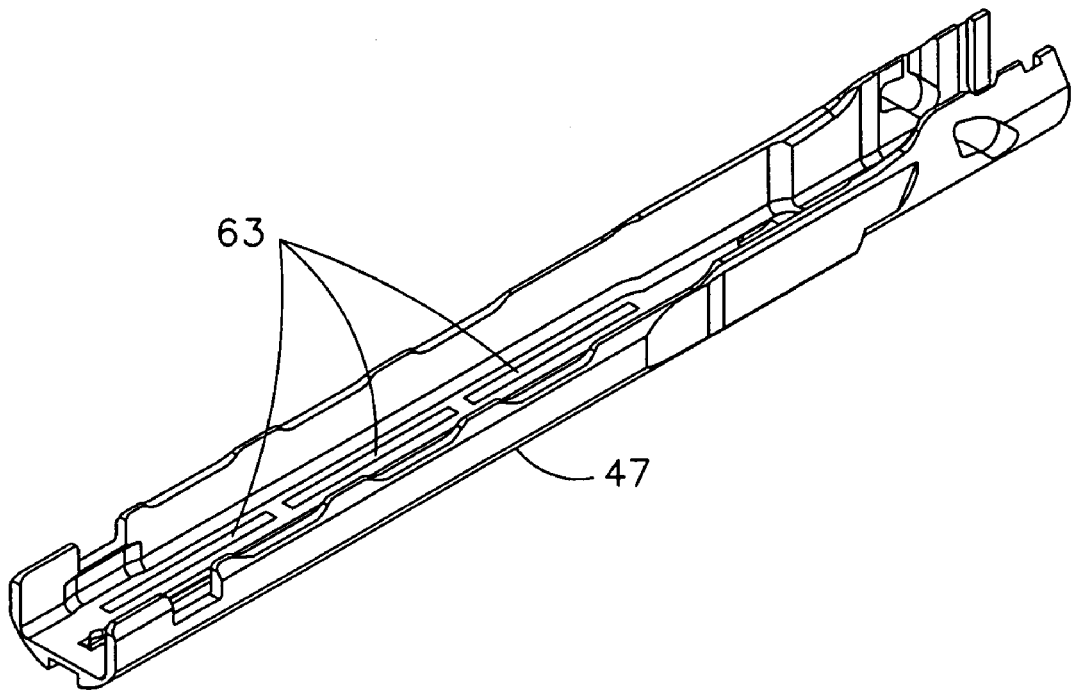
FIG. 4 is a left front isometric view of the elongate staple channel of the staple applying assembly of FIG. 1 incorporating an aligned series of EAP sensor strips for load sensing.
Figure 5:
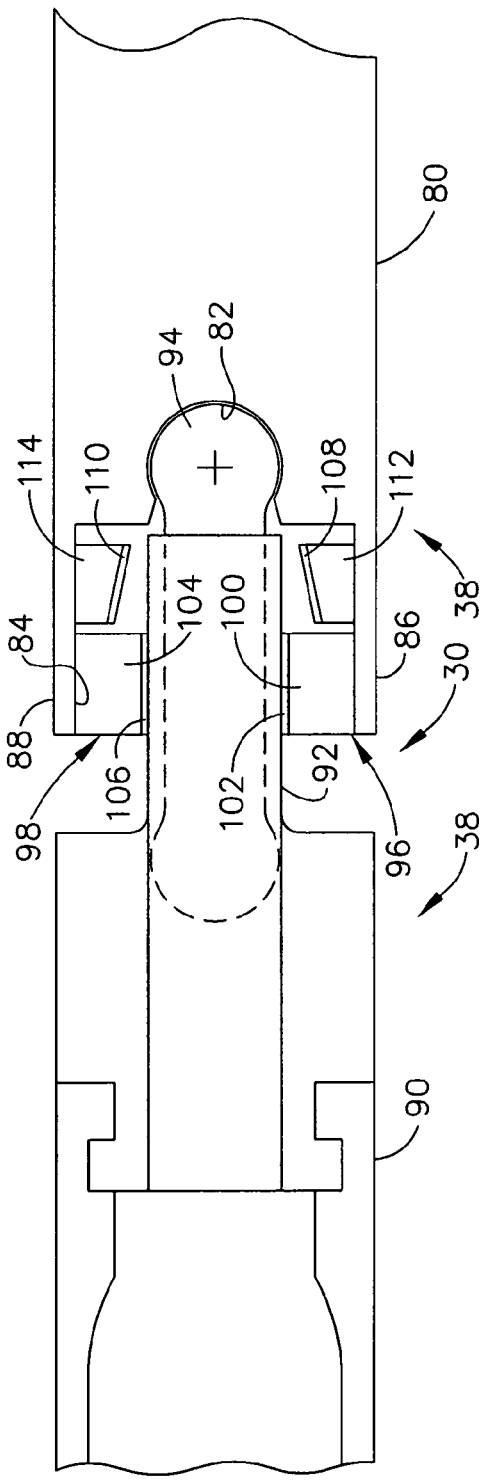
FIG. 5 is a top view of an articulation joint of a frame ground assembly of an elongate shaft of the surgical stapling and severing instrument of FIG. 1.
Figure 6:
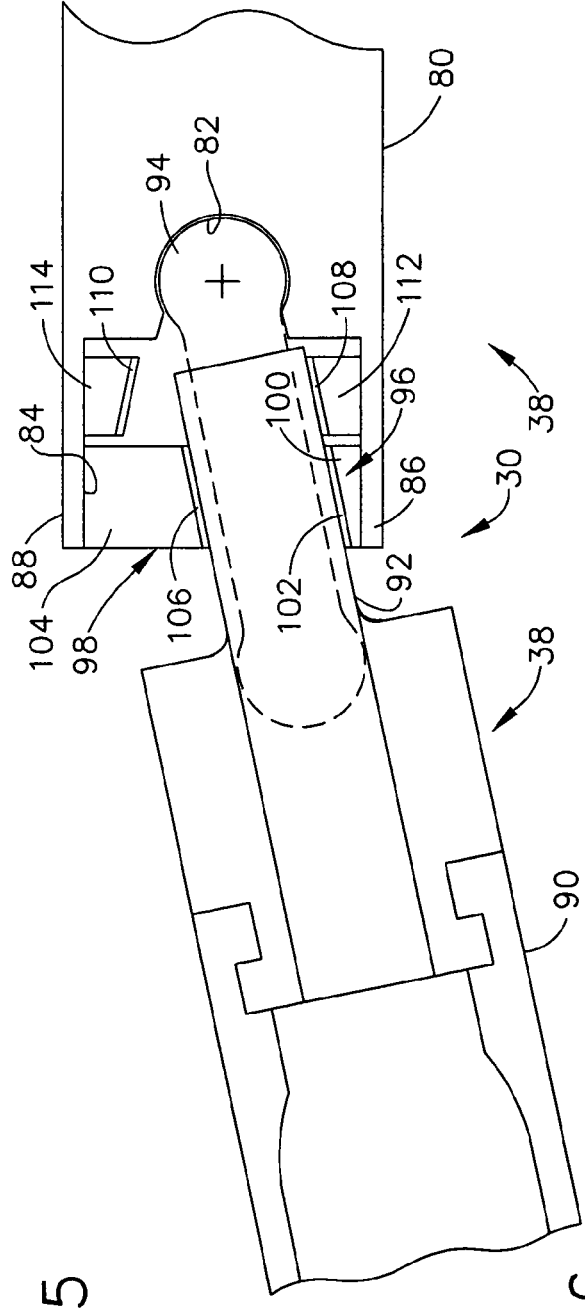
FIG. 6 is a top view of the articulation joint of FIG. 5 in a leftward articulated state.

In FIGS. 4-5, an illustrative articulation joint 30 includes a proximal frame ground portion 80 of the frame ground assembly 38 has a cylindrical pin recess 82 that communicates with a vertical recess 84 formed between left and right distally projecting frame arms 86, 88. A distal frame ground portion 90 of the frame ground assembly 38 includes a tapered, proximally projecting arm 92 that terminates in a cylindrical pin 94 pivotally received within the cylindrical pin recess 82 of the proximal frame ground portion 80.

In a distal portion of the vertical recess 84, left and right actuating/sensing EAP laminate stacks 96, 98 are inserted on respective sides of the tapered, proximally projecting arm 92 attached respectively to the left and right distally projecting frame arms 86, 88. The left actuating/sensing EAP laminate stack 96 comprises a left EAP articulation actuator 100 with a left thin EAP pressure sensor 102 attached across its inner surface against the tapered, proximally projecting arm 92. Similarly, the right actuating/sensing EAP laminate stack 98 comprises a right EAP articulation actuator 104 with a right thin EAP pressure sensor 106 attached across its inner surface against the tapered, proximally projecting arm 92. As a selected EAP articulation actuator 104 is activated (expands), a pressure reading may be sensed by the left and/or the right thin EAP pressure sensors 102, 106, representative of the articulation angle of the articulation joint 30.

Alternatively or in addition to continuous articulation angle sensing, left and right thin EAP limit sensors 108, 110 are positioned in a proximal portion of the vertical recess 84 on respective left and right pivot stops 112, 114 angled to abut the tapered, proximally projecting arm 92 at a maximum allowed articulation angle.

Returning to FIGS. 1-2, the controller 60 also receives signals from a firing bar sensor 120 that detects distal firing travel. The controller 60 may thus advantageously activate a buttress deployment system 121, (e.g., upper and lower buttress clamps 48, 50) described in co-pending and commonly owned U.S. patent application Ser. No. 11/181,471 entitled "Surgical Stapling Instrument Having an Electroactive Polymer Actuated Buttress Deployment Mechanism" and filed on Jul. 14, 2005, the disclosure of which is hereby incorporated by reference in its entirety, to automatically deploy the buttress pads 42, 44 after firing. Alternatively or in addition, the controller 60 may thus advantageously activate a medical substance dispensing actuator 122 during firing to enhance a therapeutic result (e.g., coagulant, adhesive, antibiotic, etc.), such as described in co-pending and commonly owned U.S. patent application Ser. No. 11/157,767 entitled "Surgical Stapling Instrument Having an Electroactive Polymer Actuated Medical Substance Dispenser" and filed on Jun. 1, 2005, the disclosure of which is hereby incorporated by reference in its entirety. Alternatively or in addition, the controller 60 may thus advantageously selectively enable and/or disable an anti-backup actuator 123 at the end of the firing stroke to allow for automatic retraction, as described in co-pending and commonly owned U.S. patent application Ser. No. 11/181,046 entitled "Anti-Backup Mechanism for a Multi-Stroke Endeffector Using Electrically Active Polymers" and filed on Jul. 14, 2005, the disclosure of which is hereby incorporated by reference in its entirety.

In FIGS. 7-10, the firing bar sensor 120 comprises an EAP stack actuator that is positioned within an alternative elongate shaft 124 to contact a portion of the firing member as full firing travel is reached. In particular, the firing member comprises a clevis 126 at a distal end of a firing rod 34 that receives an upwardly hooked end 128 of the firing bar 36. The laterally widened profile of the clevis 126 hits the firing bar sensor 120, which is attached inside of a firing member slot 130 formed inside of the frame ground assembly 38.

Figure 7:
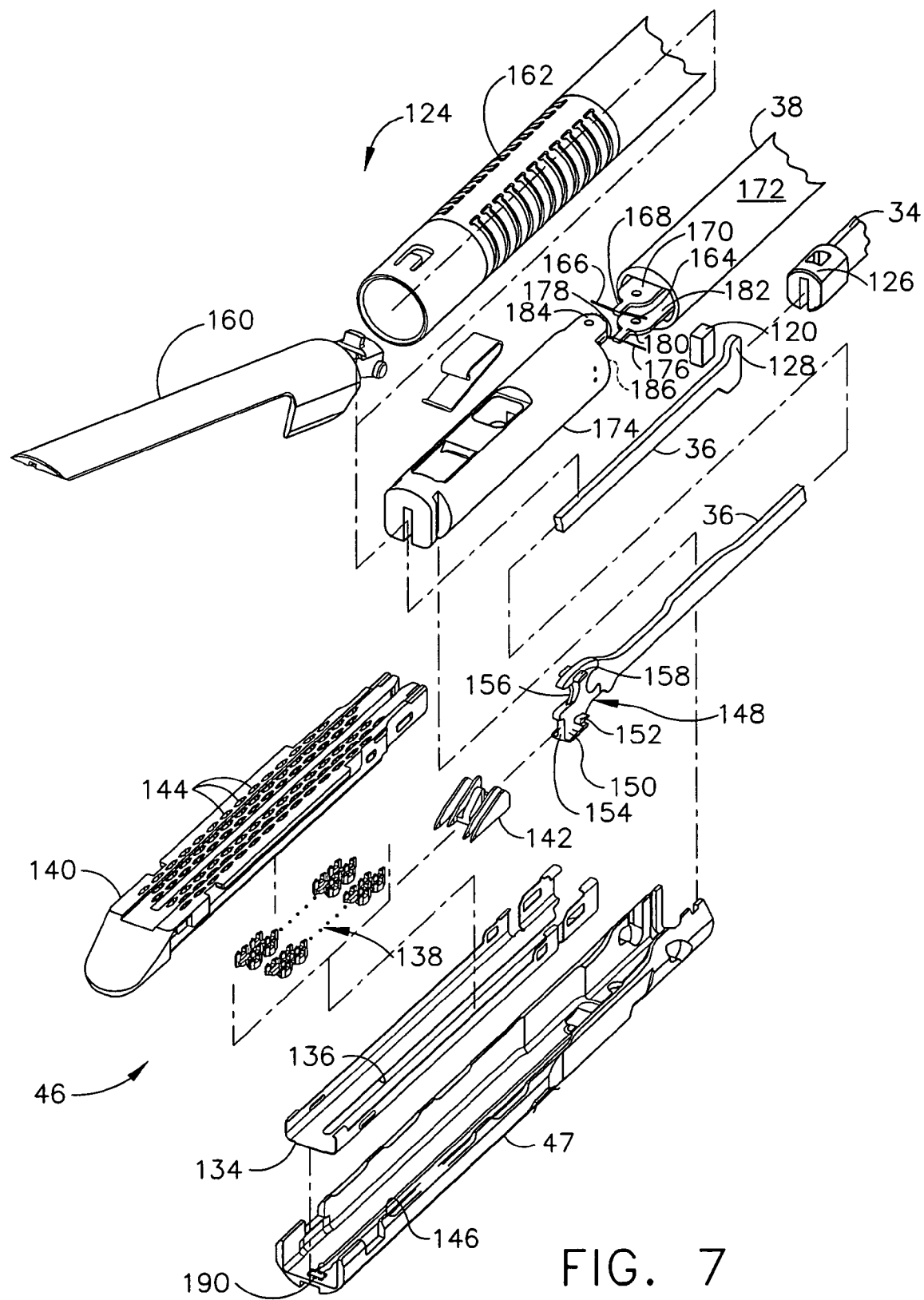
FIG. 7 is a isometric exploded view of an elongate shaft incorporating a firing bar sensor for the surgical stapling and severing instrument of FIG. 1, omitting a buttress deployment system and including alternate EAP fiber articulation actuators.

In FIG. 7, the staple cartridge 46 includes a bottom tray 134 with a proximally open longitudinal slot 136. A plurality of staple drivers 138 sit upon the bottom tray 134 on either side of the longitudinal slot 136, upon which in turn sit a plurality of staples (not shown). A staple body 140 sits down upon the staple drivers 138, providing suitable recesses (not shown) for the staple drivers 138 to be actuated upward by a distally driven wedge sled 142 ejecting the staples from staple apertures 144 formed in the staple body 140. The assembled staple cartridge 46 is received in the elongate staple channel 47 with the proximally open longitudinal slot 136 in the bottom tray 134 vertically aligned with a channel slot 146 in the elongate staple channel 47.

Figures 8, 9:
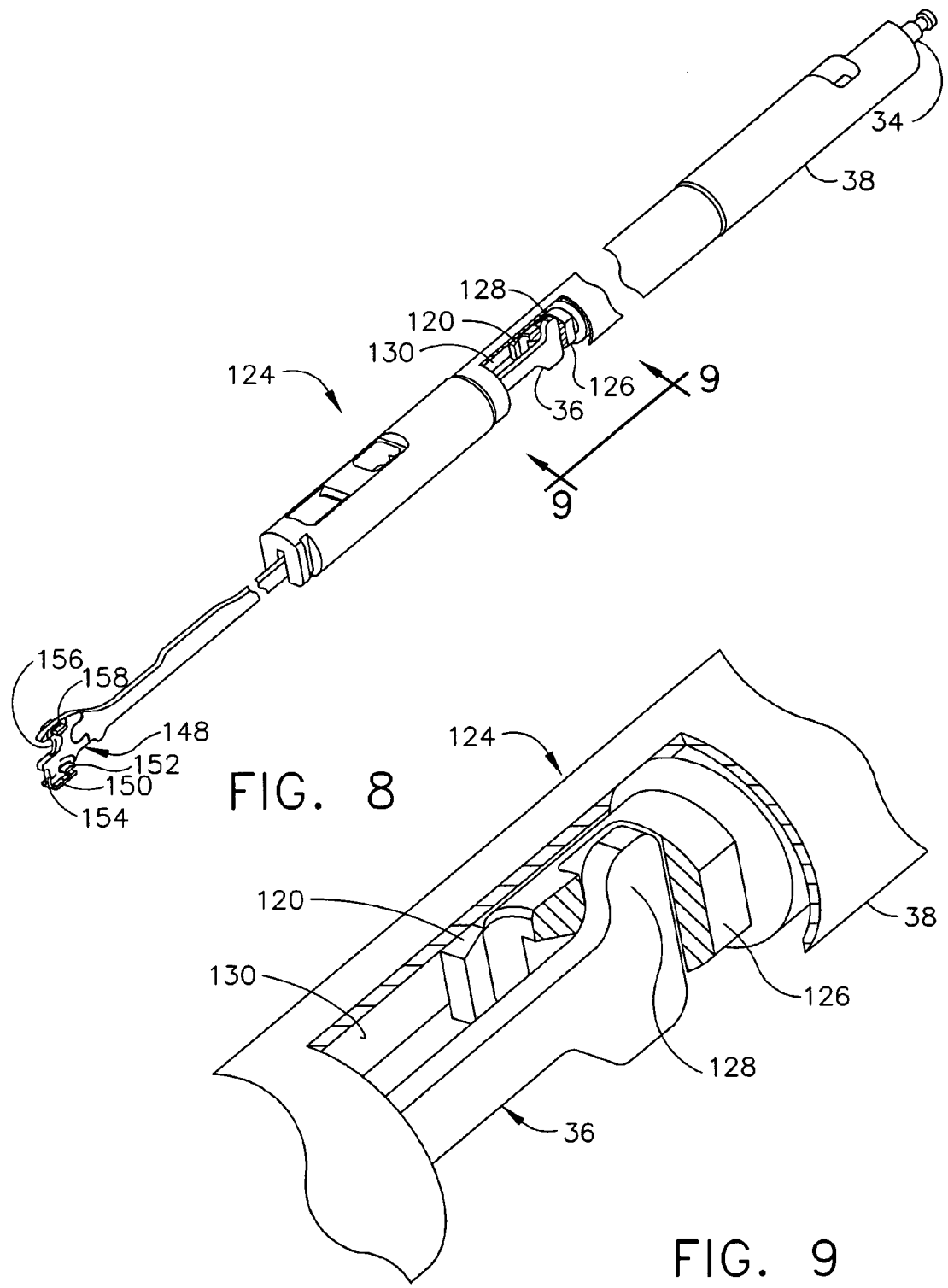
FIG. 8 is an isometric view of the elongate shaft of the surgical stapling and severing instrument of FIG. 7 with a closure sleeve and staple applying assembly omitted to expose the firing bar sensor and firing bar.
FIG. 9 is an isometric detail view of a proximal end of the firing bar activating the firing bar sensor in the elongate shaft of the surgical stapling and severing instrument of FIG. 8.

In FIGS. 7-8, the distal end of the firing bar 36 is an E-beam 148 having a lower foot 150 that slides along a bottom surface of the elongate staple channel 47 as a middle pin 152 slides along a top surface of the bottom tray 134 inside of the staple cartridge 46. A distal driving surface 154 of the E-beam 148 abuts and drives the wedge sled 142. Above the distal driving surface 154, a recessed cutting surface 156 traverses along and above a top surface of the staple cartridge 46 to cut tissue. A top pin 158 of the E-beam 148 engages an anvil (upper jaw) 160 (which omits buttress clamps) to maintain spacing. An alternative flexing closure sleeve 162 encompasses the frame ground assembly 38.

With particular reference to FIG. 7, articulation differs from the previously described version in that upper left and right EAP fiber articulation actuators 164, 166 are attached at their inner ends to an upper articulation arm 168 that projects from an upper distally projecting tang 170 from a proximal frame ground portion 172 with outer ends attached to respective opposite inner surfaces of a distal frame ground portion 174. Similarly, lower left and right EAP fiber articulation actuators 176, 178 are attached at their inner ends to a lower articulation arm 180 that projects from a lower distally projecting tang 182 from the proximal frame ground portion 172 with outer ends attached to respective opposite inner surfaces of the distal frame ground portion 174. Upper and lower proximally projecting tangs 184, 186 from the distal frame ground portion 174 are pinned for rotation respectively to the upper and lower distally projecting tangs 170, 182 of the proximal frame ground portion 172.

Figure 10:
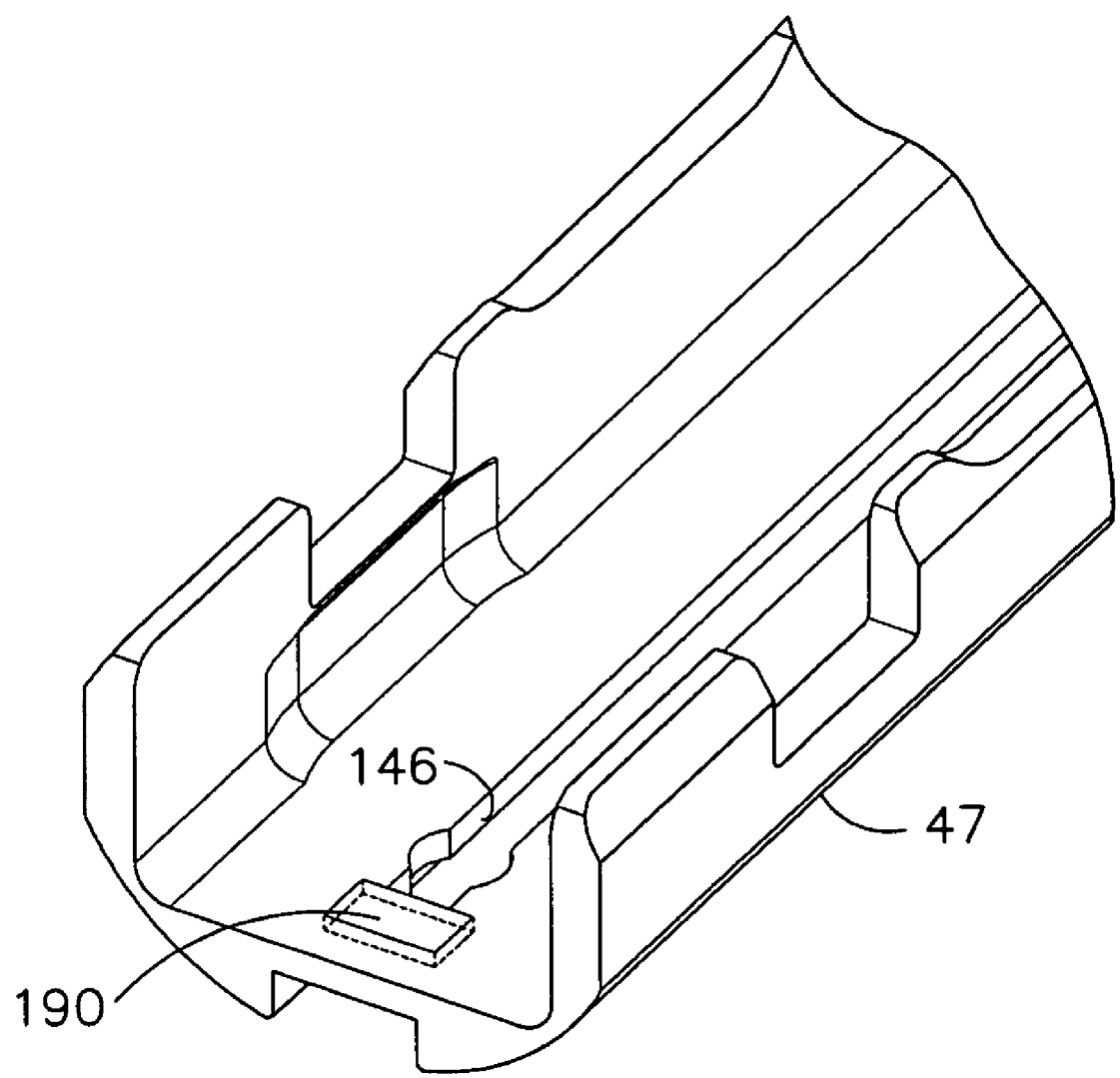
FIG. 10 is a detail view of a distal portion of an elongate staple channel of FIG. 8 including an alternative firing bar sensor positioned at a distal end of a firing bar channel slot.

In FIGS. 7, 10, alternatively or in addition to a proximally positioned firing bar sensor 120, a distally positioned EAP pressure sensor 190 may be positioned on the elongate staple channel 47 to contact the wedge sled 142 upon full distal travel.

Figure 11:
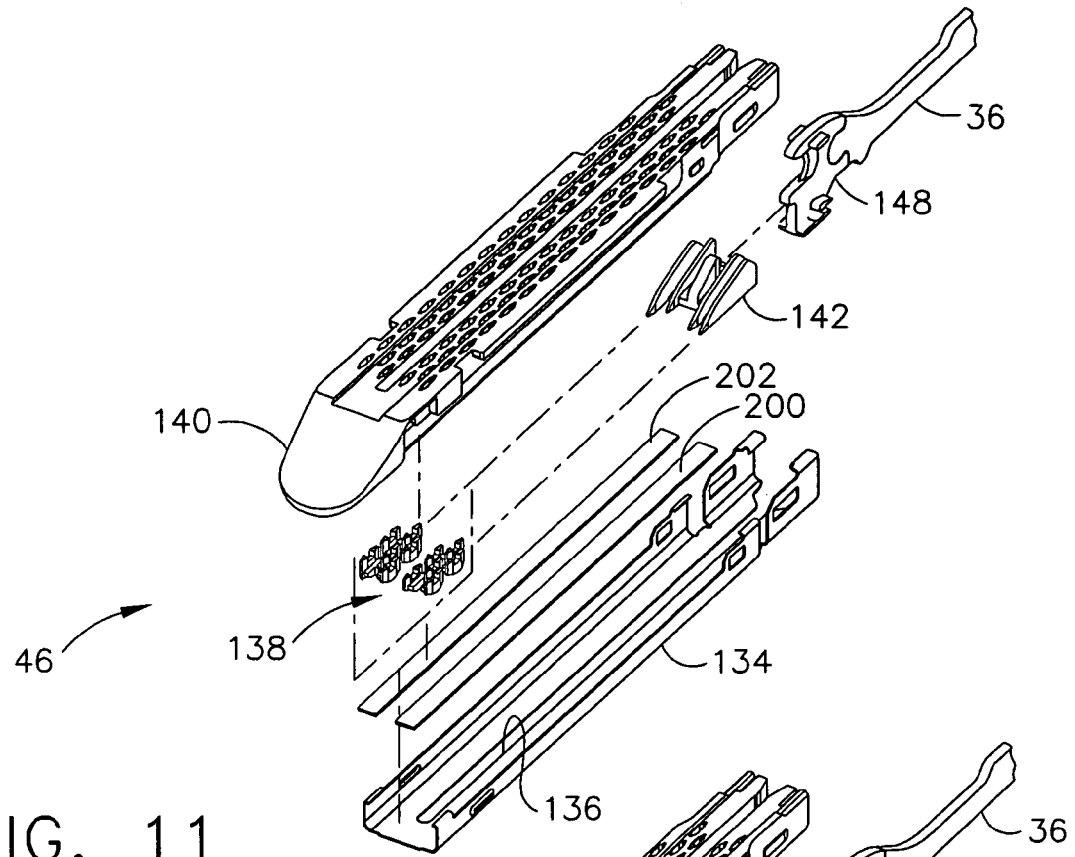
FIG. 11 is an isometric exploded view of an alternative staple cartridge incorporating elongate EAP pressure sensors positioned to detect staple driving for the surgical stapling and severing instrument of FIG. 1.
Figure 12:
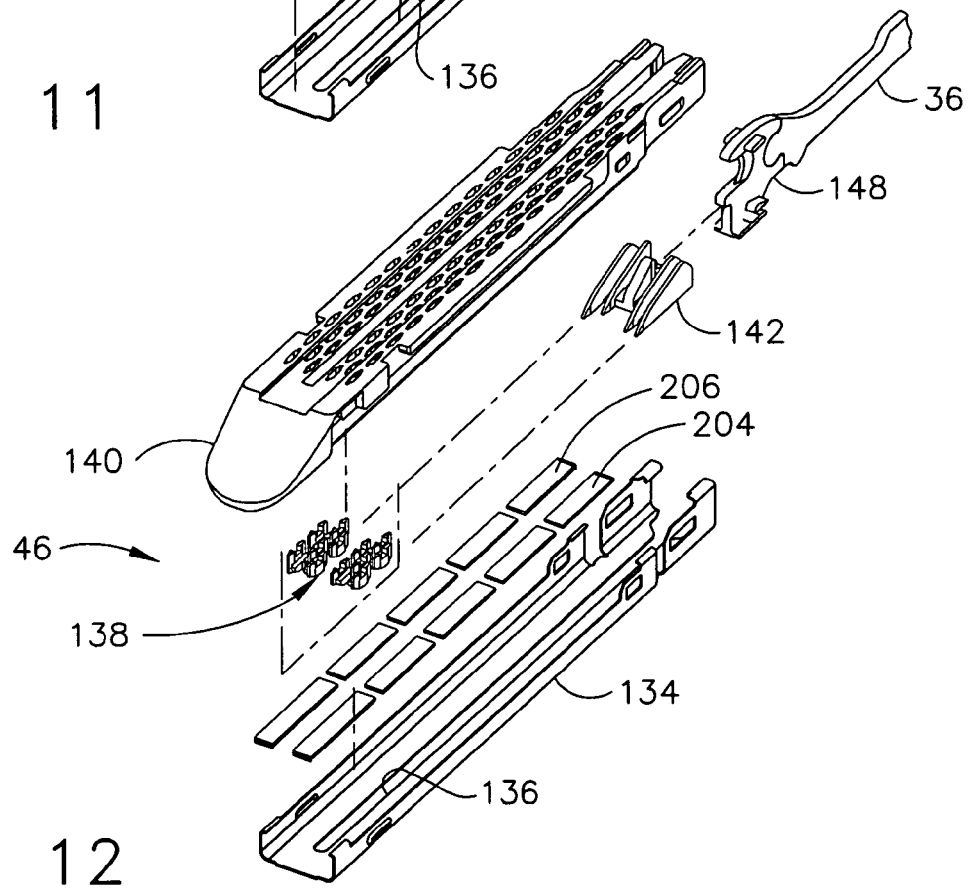
FIG. 12 is an isometric exploded view of an additional alternative staple cartridge incorporating an aligned series of EAP pressure sensors positioned to detect staple driving for the surgical stapling and severing instrument of FIG. 1.
Figure 13:
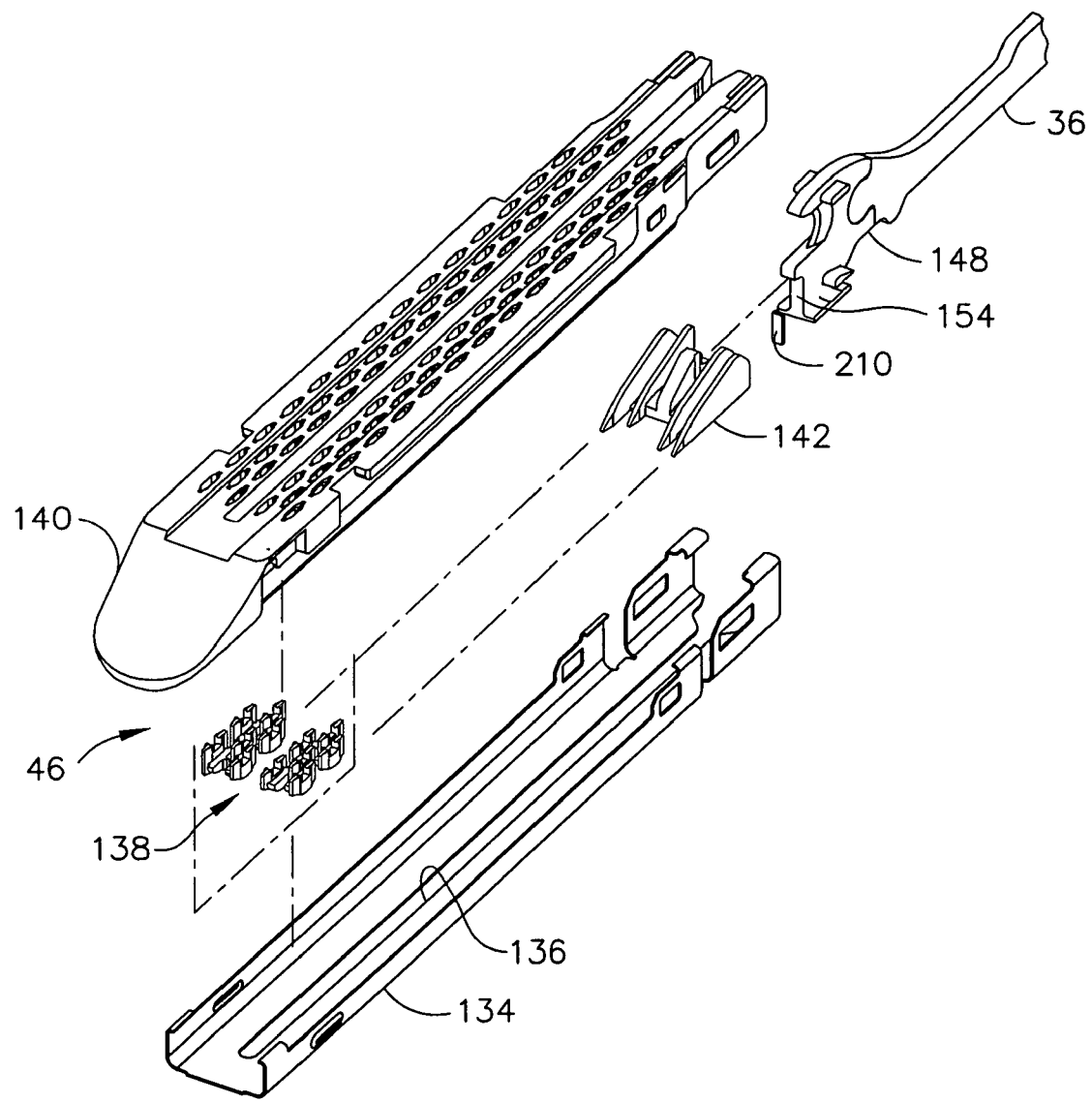
FIG. 13 is an isometric exploded view of the staple cartridge and a distal portion of the firing bar having a distal EAP pressure sensor positioned to abut a wedge sled that drives staples during firing for the surgical stapling and severing instrument of FIG. 1.

In FIG. 11, left and right elongate EAP pressure sensors 200, 202 are placed on each side of the longitudinal slot 136 in the bottom tray 134 to sense the progress of the wedge sled 142 during firing. In FIG. 12, a series of left and right EAP pressure sensors 204, 206 are placed on each side of the longitudinal slot 136 on the bottom tray 134. In FIG. 13, alternatively or in addition, a firing bar sensor is depicted as an EAP pressure sensor 210 placed on the distal driving surface 154 of the E-beam 148 to register a force during firing, especially an increase in sensed force when the wedge sled 142 reaches full distal travel.

It should be appreciated given the benefit of the present disclosure that a firing sensor may be incorporated into a handle instead of or in addition to a firing bar sensor in the implement portion 14. An illustrative version of the handle portion 12 without the closed loop control system 55 is described in U.S. patent application Ser. Nos. 11/052,387 entitled "Surgical Stapling Instrument Incorporating A Multi-Stroke Firing Mechanism With Return Spring Rotary Manual Retraction System" to Shelton et al., filed on Feb. 7, 2005, the disclosure of which is hereby incorporated by reference in its entirety.

It should be appreciated given the benefit of the present disclosure that a controller 60 may comprise a microcontroller with memory containing a program that monitors sensors and generates control signal(s) for electrically activated components. Alternatively, a controller 60 may comprise a programmable logic array, lumped component logic gates, optical logic components, or other electronic circuitry. In addition portions of a closed loop control system 55 consistent with aspects of the invention may be remote to the surgical stapling and severing instrument 10.

ELECTROACTIVE POLYMERS. While a number of electrical actuators (e.g., solenoids) may be integrated into the surgical stapling and severing instrument 10, illustrative versions described herein advantageously employ electroactive polymers (EAP), which are conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material is manufactured by Santa Fe Science and Technology, is sold as PANION™ fiber and is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is from Artificial Muscle Inc, a division of SRI Laboratories. Plate EAP material is also available from EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while EAP actuator and sensors are described as having advantageous features, applications consistent with the present invention may incorporate other types of actuators and electrical transducers For another example, while a manually operated surgical stapling and severing instrument 10 is depicted for clarity, it should be appreciated that robotically manipulated and/or controlled fastening devices may incorporate load sensing transducers for closed control and/or monitoring. Such sensors may be particularly useful to replace tactile feedback to a surgeon.

As yet another example, while a surgical stapling and severing instrument particularly suited for endoscopic or laparoscopic use is illustrated herein, applications consistent with aspects of the present invention may be for open surgical use or perform similar surgical procedures. In additions, a circular stapler may incorporate electrical sensors and/or electrical actuators for purposes such as load sensing.

For yet another example, applications consistent with the present invention may include various combinations of the sensors and/or actuators described herein. For instance, a fully mechanical closure and firing system may include electrical sensors that are monitored by a controller and a status displayed. The surgeon thus "closes the loop" by discontinuing if a warning is presented. In addition, certain features may be omitted such as articulation or buttressing.

As yet a further example, although separate closure and firing mechanisms, including separate triggers, are described in the illustrative versions, applications consistent with the present invention may incorporate a single firing trigger that sequentially effects closure and firing.

As yet an additional example, while EAP pressure sensors are an advantageous way to sense clamping, firing and articulation, other electrical sensors may be incorporated in addition to or in the alternative, such as proximity sensors (e.g., Hall effect), capacitive sensors, microswitches, and position sensors (e.g., potentiometers).

What is claimed is:

1. A surgical instrument, comprising:
   an end effector comprising first and second opposing compression surfaces;
   a shaft proximally attached to the end effector;
   a handle portion proximally attached to the shaft comprising an actuating mechanism operatively coupled through the shaft to selectively actuate the end effector;
   a pressure transducer positioned to receive a compression load when the end effector is actuated; and
   control circuitry responsive to a signal received from the pressure transducer to generate a control signal.

2. The surgical instrument of claim 1, further comprising an indicator attached to the handle portion activated by the control signal.

3. The surgical instrument of claim 1, wherein the actuating mechanism comprises a closure mechanism operatively configured to selectively close the first and second opposing compression surfaces upon tissue, the pressure transducer positioned in the end effector to receive a compressive load.

4. The surgical instrument of claim 3, further comprising a firing member received for longitudinal reciprocation in the shaft, wherein the end effector comprises a staple applying assembly responsive to movement of the firing member to sever and staple clamped tissue.

5. The surgical instrument of claim 4, further comprising a firing lockout mechanism responsive to the control signal from the control circuitry to prevent firing, wherein the control circuitry is operatively configured to generate the control signal in response to a comparison between the sensed compressive load and a threshold value.

6. The surgical instrument of claim 1, further comprising a firing member received for longitudinal reciprocation in the shaft, wherein the end effector comprises a staple applying assembly responsive to movement of the firing member to sever and staple clamped tissue.

7. The surgical instrument of claim 6, wherein the pressure transducer is positioned proximate to the firing member to receive a compressive load representative of firing.

8. The surgical instrument of claim 7, wherein the firing member comprises a laterally expanded portion positioned for longitudinal translation within a recess defined in the shaft, the pressure transducer attached within the recess in the shaft to contact the expanded portion of the firing member approaching full firing travel of the firing member.

9. The surgical instrument of claim 7, wherein the firing member comprises a wedge positioned for translation in the staple applying assembly, the pressure transducer positioned in the staple applying assembly to receive a compressive load in response to the firing member distally translating the wedge to dispense and form staples through clamped tissue.

10. The surgical instrument of claim 9, wherein the pressure transducer is positioned at a distal end of the staple applying assembly to contact the wedge at full firing travel.

11. The surgical instrument of claim 9, wherein the pressure transducer is positioned at an intermediate longitudinal portion of firing travel of the wedge on a surface underlying the wedge.

12. The surgical instrument of claim 9, wherein the pressure transducer comprises a plurality of longitudinally aligned pressure transducers registered along full firing travel of a portion of the wedge.

13. The surgical instrument of claim 9, wherein the pressure transducer comprises an elongate pressure sensor registered on an undersurface contacted by the wedge during full firing travel.

14. The surgical instrument of claim 9, wherein the firing member further comprises a firing bar having a contact surface that proximally abuts the wedge, the pressure transducer attached to the contact surface of the firing bar.

15. The surgical instrument of claim 1, wherein the shaft further comprises an articulation joint, the actuating mechanism comprises an articulation mechanism operatively configured to actuate the end effector by rotating the end effector about the articulation joint, the pressure sensor positioned to receive a compressive force from the articulation mechanism representative of an articulation angle of the articulation joint.

16. The surgical instrument of claim 15, wherein the pressure transducer comprises a limit sensor.

17. The surgical instrument of claim 15, wherein the pressure transducer comprises a continuous angle sensor.

18. The surgical instrument of claim 15, further comprising an electrical articulation actuator, the control circuitry operatively configured to respond to the sensed articulation angle to control the electrical articulation actuator.

19. The surgical instrument of claim 15, further comprising an electrical articulation lock actuator, the control circuitry operatively configured to respond to the sensed articulation angle to control the electrical articulation lock actuator.

20. The surgical instrument of claim 1, wherein the pressure transducer comprises an electroactive polymer pressure transducer.

21. A surgical instrument, comprising:
a staple applying assembly comprising first and second opposing compression surfaces;
a shaft proximally attached to the staple applying assembly;
a firing member received for longitudinal reciprocation in the shaft;
a handle portion proximally attached to the shaft operatively coupled through the shaft to close the first and second opposing compression surfaces upon tissue and to translate the firing member to actuate the staple applying assembly;
an electrical actuator responsive to a command signal;
a pressure transducer positioned to receive a compression load when the end effector is actuated; and
control circuitry responsive to a signal received from the pressure transducer to generate the control signal.

22. The surgical instrument of claim 21, wherein the electrical actuator comprises a buttress deployment actuator.

23. The surgical instrument of claim 21, wherein the electrical actuator comprises a firing lockout mechanism coupled to the firing member to disable firing in response to the control signal.

24. A surgical instrument, comprising:
an end effector;
a shaft proximally attached to the end effector;
a firing member received for longitudinal reciprocation in the shaft;
a handle portion proximally attached to the shaft and operatively configured to translate the firing member to actuate the end effector;
a pressure transducer positioned to receive a compression load in response to a translation of the firing member; and
control circuitry responsive to a signal received from the pressure transducer to generate a control signal.

25. The surgical instrument of claim 24, further comprising a resilient retraction bias on the firing member and an electrical anti-backup actuator responsive to the control signal to allow retraction of the firing member by the resilient retraction bias.

26. The surgical instrument of claim 24, further comprising an electrically activated medical substance delivery actuator responsive to the control signal to dispense a medical substance at the end effector.

27. The surgical instrument of claim 24, wherein the end effector comprises a staple applying assembly, the surgical instrument further comprising an electrically activated buttress deployment actuator responsive to the control signal to deploy buttress material from the staple applying assembly.

28. A surgical instrument, comprising:
an end effector;
a shaft proximally attached to the end effector;
an articulation joint formed in the shaft;
a pressure transducer positioned to receive a compression load in response to articulation movement of the articulation joint; and
control circuitry responsive to a signal received from the pressure transducer to generate a control signal.

29. The surgical instrument of claim 28, further comprising an articulation actuator coupled to the articulation joint to effect articulation movement, wherein the control circuitry is operatively configured to generate the control signal in comparison to a commanded articulation angle compared to a sensed compression load from the pressure transducer.

30. The surgical instrument of claim 28, further comprising an electrically activated articulation joint lock responsive to the control signal to selectively lock the articulation joint at a current articulation angle.

* * * * *